(12) United States Patent
Parker et al.

(10) Patent No.: US 11,719,611 B2
(45) Date of Patent: Aug. 8, 2023

(54) METHOD FOR PRODUCING A VOID FRACTION ERROR CURVE USING A DEVICE TO MEASURE A PROPERTY OF A MULTI-PHASE FLOW

(71) Applicant: M-Flow Technologies Limited, Abingdon (GB)

(72) Inventors: Alan David Parker, Abingdon (GB); Giles Edward, Abingdon (GB)

(73) Assignee: M-Flow Technologies Limited, Abingdon (GB)

( * ) Notice: Subject to any disclaimer, the term of this patent is extended or adjusted under 35 U.S.C. 154(b) by 207 days.

(21) Appl. No.: 17/276,466

(22) PCT Filed: Sep. 11, 2019

(86) PCT No.: PCT/GB2019/052531
§ 371 (c)(1),
(2) Date: Mar. 15, 2021

(87) PCT Pub. No.: WO2020/053581
PCT Pub. Date: Mar. 19, 2020

(65) Prior Publication Data
US 2022/0034777 A1    Feb. 3, 2022

(30) Foreign Application Priority Data

Sep. 13, 2018    (GB) ...................................... 1814910

(51) Int. Cl.
*G01N 9/36* (2006.01)
*G01F 25/10* (2022.01)
(Continued)

(52) U.S. Cl.
CPC ................. *G01N 9/36* (2013.01); *G01F 1/40* (2013.01); *G01F 1/74* (2013.01); *G01F 1/8436* (2013.01);
(Continued)

(58) Field of Classification Search
None
See application file for complete search history.

(56) References Cited

U.S. PATENT DOCUMENTS

| 5,861,561 A | 1/1999 | Van Cleve et al. |
| 7,363,800 B2 | 4/2008 | Gysling |

(Continued)

FOREIGN PATENT DOCUMENTS

| WO | WO 97/26509 | 7/1997 |
| WO | WO2004/072588 A2 | 8/2004 |

(Continued)

OTHER PUBLICATIONS

Mills, Chris, "Correcting a Coriolis Meter for Two Phase Oil & Gas Flow," International Flow Measurement Conference, University of Warwick, U.K. Jul. 1-2, 2015.

(Continued)

*Primary Examiner* — Harshad R Patel
(74) *Attorney, Agent, or Firm* — Levy & Grandinetti

(57) ABSTRACT

A method produces a void fraction (VF) error curve which correlates an apparent VF with the actual VF of a multi-phase flow, the method comprising (a) using a device to measure a property of the multi-phase flow from which an apparent VF may be calculated; (b) calculating the apparent VF using the measured property from the device; (c) determining the actual VF of the multiphase flow using a radiometric densitometer; (d) using the values from steps (b) and (c) to calculate the VF error; (e) repeating steps (b) through (d) for all expected flow conditions to generate a VF error curve.

18 Claims, 7 Drawing Sheets

(51) Int. Cl.
    *G01F 1/40*     (2006.01)
    *G01F 1/74*     (2006.01)
    *G01F 1/84*     (2006.01)
    *G01N 9/00*     (2006.01)
    *G01N 22/00*     (2006.01)
    *G01N 23/12*     (2018.01)
    *G01N 33/28*     (2006.01)

(52) U.S. Cl.
    CPC ............ *G01F 25/10* (2022.01); *G01N 9/002* (2013.01); *G01N 22/00* (2013.01); *G01N 23/12* (2013.01); *G01N 33/2841* (2013.01)

(56) References Cited

U.S. PATENT DOCUMENTS

| | | | | |
|---|---|---|---|---|
| 7,380,438 | B2* | 6/2008 | Gysling | G01N 33/2823 |
| | | | | 73/19.1 |
| 8,641,813 | B2* | 2/2014 | Gysling | G01F 1/666 |
| | | | | 96/417 |
| 10,533,955 | B2 | 1/2020 | Parker et al. | |
| 2007/0239402 | A1* | 10/2007 | Scott | G01N 22/00 |
| | | | | 702/22 |
| 2014/0224006 | A1 | 8/2014 | Scott | |

FOREIGN PATENT DOCUMENTS

WO      WO 2005/116637      12/2005
WO      WO 2016/135506      9/2016

OTHER PUBLICATIONS

Thorn R. et al.: Review Article: Recent developments in three-phase flow measurement, Measurement Science and Technology, IOP, Bristol, GB, vo. 8, No. 7, Jul. 1, 1997, pp. 691-701. XP020064292.

* cited by examiner

METHOD FOR PRODUCING A VOID FRACTION ERROR CURVE USING A DEVICE TO MEASURE A PROPERTY OF A MULTI-PHASE FLOW

FIELD OF THE INVENTION

The present invention relates to a method for calibrating a void fraction measurement made in relation to a multi-phase flow and to a method and apparatus for calculating the mass flow rate of one or more phases in a multiphase flow.

DESCRIPTION OF THE RELATED ART

The extraction of hydrocarbons is known to present many challenges. One of the challenges is to establish the phase fractions of the materials extracted from a well, when the flow of extracted materials may comprise up to three phases (a liquid oil phase, a liquid aqueous phase and a gaseous phase). Not only may the volume fractions of the phases change with time, but the distribution of the phases in the flow may also change. In particular, the distribution of any gaseous phase present may change as a result of the flow environment, the presence of bends in the pipe and other factors. Part of the flow may comprise a relatively homogenous distribution of small bubbles, while in another part the coalescence of gas bubbles may result in a heterogeneous distribution of the gaseous phase. Changes in the pressure and temperature may also cause materials, such as volatile hydrocarbons, to move between the liquid and gaseous phases. It is important to know the mass flow rate of the extracted hydrocarbons, since oil extraction is the whole purpose of the business.

One method of addressing this problem is to provide flow meters downstream of two or three-phase separator(s), then separately to measure the flow of each of the phases. The separators may be large, expensive and maintenance-intensive. In addition, if the separator(s) are incorrectly sized, then a materially significant amount of gas may remain entrained in the output liquid phase(s) or water in the oil output of a three phase separator. Separator sizing requirements can change as a well ages and it is often not practical or economically viable to replace a separator during the life of an individual well.

Multiphase meters capable of determining the phase volume fractions may employ several different measurement methods to achieve the objective. One such method involves using a device which is sensitive to changes in the permittivity of the flow, such as a microwave resonator and, separately, measuring the density of the combined flow. An apparatus suitable for carrying out these measurements is disclosed in WO 2016/135506 A1 and involves passing the fluid flow through a resonant cavity microwave meter and additionally measuring the bulk density of the flow by means of a gamma densitometer.

Radiometric densitometers, such as gamma and x-ray densitometers, although accurate, require the use of a hazardous radioactive source, which in turn gives rise to health and safety concerns and necessitates significant shielding. This can make such meters heavy, cumbersome and costly. In addition, special certification and other procedures are needed before a radioactive source may be used on site, which are time-consuming and costly to organize.

Coriolis meters are known for the measurement of mass flow rate and density. Such meters comprise tubes that are vibrated at their natural frequency. When no flow is present, the tubes vibrate in phase and show no sign of twist. Once a flow is introduced, Coriolis forces give rise to a twisting effect in the tubes. By measuring the time shift in phase of oscillation of each measuring tube, a mass flow rate may be calculated, and by measuring the natural frequency of oscillation of one of the measuring tubes, the density may be calculated.

In principle, Coriolis meters represent a safer and less bulky alternative to radiometric densitometers for measuring the bulk density of a flow and they have the additional benefit of measuring the mass flow rate as well. In practice, however, Coriolis meters may give inaccurate readings of both bulk density and mass flow rate if there are phases of significantly different density and/or viscosity present such that there is poor coupling between the dispersed and continuous phases, an effect which may be referred to as "phase contamination". The problem may be especially significant when the flow comprises mixtures of liquid and gaseous phases. The introduction of gas into a liquid flowing through a Coriolis meter significantly dampens the amplitude and distorts the phase of the tube oscillations. These changes lead to errors in both the mass flow and the density data from the meter. In general, the measurement error is dependent upon a number of parameters, such as the liquid velocity and viscosity, the pressure and temperature of the flow and the degree of entrainment of the gas in the liquid. If the gas decouples from the liquid, such that it is no longer entrained, then so-called "slug flow" may result, which may increase the measurement errors. These factors, which are all variable, may make it difficult to compensate for the measurement errors in the field. Reference may be made to the paper by Chris Mills entitled "Correcting a Coriolis Meter for Two Phase Oil & Gas Flow", presented at the International Flow Measurement Conference 2015 from 1-2 Jul. 2015 at the University of Warwick, UK.

For 3-phase flow in hydrocarbon extraction (comprising an oil phase, a water phase and a gaseous phase), if the gas to liquid ratio and the fluid velocity is relatively constant and known, then an approximate correction factor may be applied which may allow the Coriolis meter to output a relatively accurate density and mass flow rate. If, on the other hand, these quantities fluctuate significantly, then this approach does not provide an accurate bulk density and mass flow rate.

It is against this background that the present invention has been devised.

SUMMARY OF THE INVENTION

According to a first aspect of the invention, a method is provided of producing a void fraction (VF) error curve which correlates an apparent VF with the actual VF of a multi-phase flow, the method comprising:
 a) Using a device to measure a property of the multi-phase flow from which an apparent VF may be calculated;
 b) Calculating the apparent VF using the measured property from the device;
 c) Determining the actual VF of the multiphase flow using a radiometric densitometer;
 d) Using the values from b) and c) to calculate the VF error;
 e) Repeating b)-d) for all expected flow conditions to generate a VF error curve.

As used herein, the term "VF" of a fluid flowing through a pipe, means:

VF=Volume of gas in unit volume of pipe at the prevailing conditions of temperature and pressure in the pipe. It is usually expressed as a percentage.

As used herein, the term "water cut" (WC) has the following meaning:

$$WC = \frac{\text{Volume of water in unit volume of pipe}}{\text{Volume of liquid in unit volume of pipe}}$$

at the prevailing conditions of temperature and pressure in the pipe. It is also usually expressed as a percentage.

The radiometric densitometer may suitably be any meter which measures the true density of the flow, such as a gamma densitometer or an x-ray densitometer. The radiometric densitometer may be a dual energy densitometer or a single energy densitometer.

The actual VF may be determined directly from the radiometric densitometer, if the radiometric densitometer is a dual energy or DEGRA (dual energy gamma ray attenuation) densitometer, which uses both a high energy and a low energy radiation source firstly to distinguish the gas from the liquid, then the oil from the water. If the radiometric densitometer is a single energy densitometer, then the actual VF may not be obtained directly and must be calculated. The calculation may be performed using the actual bulk density measured by the radiometric densitometer. Equation 1, below, may be used (substituting the apparent bulk density by the actual bulk density, measured by the radiometric densitometer, to give the actual VF).

According to a second aspect of the invention, a method of calculating the actual VF of a multiphase flow comprising measuring a property of the flow from which an apparent VF may be calculated, calculating the apparent VF of the multiphase flow and correcting the apparent VF using the VF error curve of the first aspect of the invention.

The method according to the first and second aspects of the invention may advantageously be used when the flow comprises a liquid phase and a gas phase. More advantageously, the liquid phase may comprise a water phase and an oil phase such that there is a 3-phase flow comprising a mixed oil and aqueous liquid phase and a gaseous phase.

According to one embodiment of the first and second aspects of the invention, the device which measures a property of the multi-phase flow from which an apparent VF may be calculated is a Coriolis meter. Coriolis meters measure an apparent bulk density and an apparent mass flow. The apparent bulk density measurement may be used to derive the apparent VF using Equation 1:

$$\text{Apparent } VF = \frac{\rho_L - \rho}{\rho_L - \rho_g} \qquad \text{Equation 1}$$

where $\rho_L$ is the density of the liquid, $\rho_G$ is the density of the gas and p is the apparent bulk density measured by the Coriolis meter.

During this calibration phase, $\rho_L$ and $\rho_G$ may be obtained by actual measurements taken from samples extracted from the flow line to determine the phase fractions and, if needed, data known to the skilled person from models, such as "PVT Models" (where "PVT" relates to pressure, volume and temperature).

According to another embodiment of the first and second aspects of the invention, the device which measures a property of the multi-phase flow from which an apparent VF may be calculated is a microwave meter. The microwave meter may use resonance (a "microwave resonator") or absorption. Preferably, the microwave meter is a microwave resonator such as disclosed in WO 2016/135506 A1. A microwave meter may measure the bulk permittivity of the multiphase flow from which an apparent VF may be derived in a fashion known to the skilled person.

The first and second aspects of the invention relate to the calibration of the device or devices from which an apparent VF may be derived. According to these aspects of the invention, the device such as a Coriolis meter and/or a microwave meter is installed in a flow line in the field and, additionally, a radiometric densitometer is also temporarily installed. The applicant's preferred approach is to calibrate the device in situ in the actual line in the field into which it is to be permanently installed. The device is calibrated for the entire operating envelope of the line in question. This means that a bulk density and VF error curves are generated for all expected full range of flow conditions seen by the line. The time required to do this will vary between wells but typically will be a number of days.

Once calibration has been performed, the device(s) may be monitored in use in the fashion discussed below to ensure continuing accuracy, so it is straightforward to verify the calibration.

Once VF error curve(s) have been generated for the device(s) in question, such as a Coriolis meter or a microwave meter, then the radiometric densitometer may be removed leaving just the device(s) which may thereafter be used together with the VF error curve(s) accurately to determine the actual VF of the multiphase flow.

According to a third aspect of the invention, a method is provided for calculating the mass flow rate of one or more of the phases in a multiphase flow comprising:

a) Using a Coriolis meter to measure the apparent bulk density of the multiphase flow;
b) Calculating a first apparent VF using the apparent bulk density from a);
c) Using a microwave meter to measure the permittivity of the multiphase flow;
d) Calculating a second apparent VF using the permittivity measurement from c);
e) Calculating the phase volume fractions of the multiphase flow using the results from b) and d);
f) Determining the actual bulk mass flow rate of the multiphase flow;
g) Calculating the mass flow rate of one or more of the phases using the values from d) and e).

According to the third aspect of the invention, a Coriolis meter measures the apparent bulk density and the apparent bulk mass flow rate of the multiphase flow. A first apparent VF is then calculated using Equation 1, above. After this, a microwave meter measures the bulk permittivity of the multiphase flow. A second apparent VF is calculated from the bulk permittivity measurement.

The two apparent VF measurements may be used to calculate the WC of the multiphase flow and therefore also the phase volume fractions (since knowing the WC and the VF allows calculation of the phase fractions). Both the bulk permittivity measurement from the microwave meter and the bulk density measurement from the Coriolis meter are sensitive to the VF and the WC of the multiphase flow. A specific pair of values from the two parameters (apparent bulk density and bulk permittivity) can be generated for a range of WC and VF values. The true WC and VF of the multiphase fluid in the meter arrangement can be determined by calculating the VF for a range of WC values from the measurement taken from each meter (one from the microwave meter and one for the Coriolis meter) and finding the water cut value for which both measurements give an identical void fraction.

This process may be represented by two curves on a two dimensional plot of WC versus VF. Each curve represents the possible values of WC and VF that could lead to a particular measurement value from either the microwave meter or bulk density data from the Coriolis meter. The true WC and VF values occur where these two curves cross.

The microwave data is predominantly sensitive to the water cut and the bulk density is predominantly sensitive to the void fraction. Thus the two curves from the different measurements are typically close to perpendicular to each other which means that the crossing point is sharply defined.

In an advantageous development, the VF error curves from the first aspect of the invention may be used for the calculation in e). In this case, a solution is found by iteration or by solving simultaneous equations so that the measurements from the Coriolis meter and the measurement from the microwave meter both yield the actual VF measured by the radiometric densitometer. On a two-dimensional plot of WC versus VF, the actual WC may then be determined.

According to the third aspect of the invention, the actual bulk mass flow rate of the multiphase flow must be calculated. The relationship between the differential pressure across an obstruction within a pipe and the mass flow rate of the material flowing through it for an incompressible fluid is known from Bernoulli's Principle. Thus one method for establishing the mass flow rate of material flowing through the pipe is by means of a differential pressure measurement across an obstruction to the flow within the pipework. Differential pressure meters based on this principle are well known and include Venturi and orifice plate devices. These may be used to measure the pressure drop along a section of a fluid flow path, for example along a length of pipe, or across a device. A Coriolis meter provides an obstruction to the flow within a pipe so the differential pressure across a Coriolis meter may be used to measure the mass flow rate through the meter.

The Bernoulli relationship between differential pressure across and the mass flow rate through an obstruction within a pipe would not be expected to apply to a multiphase flow containing a gaseous phase, as this type of fluid will be compressible. i.e. the line density will vary with pressure. However the applicant has established that, if the amount of gas present is less than 5%, preferably less than 2% and more preferably less than 1% by mass of the multiphase fluid, then the pressure drop for a given mass flow rate of liquid-only flow is the same as the pressure drop for same mass flow rate of a multiphase flow including a gaseous phase. In other words, the differential pressure is primarily dependent upon the liquid mass flow rate and is independent of the VF. Installation of a device to measure the differential pressure may therefore allow an accurate determination of the liquid mass flow rate even for a multiphase flow containing a gaseous phase.

According to the third aspect of the invention, therefore, a differential pressure meter is provided to measure the differential pressure across the Coriolis meter in order to allow the mass flow rate of the liquid within the pipe to be established.

The relationship between the mass flow rate of a liquid only flow of known density through a Coriolis meter and the differential pressure across it is an important operational parameter for many Coriolis meter installations and is likely to be known by the manufacturer. If not, it may easily be established in any case. Given that the applicant has now established that this information may be used for a multiphase flow comprising a gaseous phase, the differential pressure may advantageously be measured across the Coriolis meter and information provided with the Coriolis meter may be used to correlate the measured differential pressure across the meter with the liquid mass flow rate through it.

In order to calculate the actual mass flow rate, the actual bulk density of the multiphase flow must be known. This may be derived from a bulk density error curve which corrects the apparent bulk density measured by the Coriolis meter with the actual bulk density. A radiometric densitometer, such as that described in relation to the first aspect of the invention, may be used to measure the actual bulk density of the multiphase flow. Thus a bulk density error curve may be generated in parallel with generation of the VF error curve for the Coriolis meter according to the first aspect of the invention.

Knowing the actual bulk density from the Coriolis meter, corrected using the bulk density error curve and the phase volume fractions of the multiphase flow (generated using the Coriolis meter and the microwave meter and, advantageously, also the VF error curves of the first aspect of the invention) and the mass flow rate of the liquid using a differential pressure measurement across the Coriolis meter, the actual bulk mass flow rate may be calculated.

Using a differential pressure measurement allows the actual liquid mass flow rate to be determined in flow regimes of varying liquid phase velocity. In cases in which the liquid phase velocity is relatively constant, then there is a linear relationship between the bulk mass flow rate error and the bulk density error, so that an alternative method may be used, wherein calculating the actual bulk mass flow rate for a multiphase flow comprises:

i. determining the bulk mass flow rate error from the bulk density error; and ii. calculating the actual bulk mass flow rate by correcting the apparent bulk mass flow rate using the bulk mass flow rate error.

wherein the actual bulk density is calculated by correcting the apparent bulk density using a bulk density error curve.

Finally, according to the third aspect of the invention, the actual mass flow rate of one or more of the phases in the multiphase flow is then calculated. This is done using the phase volume fractions and the actual bulk mass flow rate. For completeness, the density of each of the individual phases at the given temperature and pressure must also be known, but this is information that the skilled person readily has available, for example from a PVT model.

Advantageously, according to the third aspect of the invention, the multiphase flow comprises water, oil and gas and the method comprises calculating the volume fractions of each of these phases. A further advantageous development according to the third aspect of the invention comprises calculating the mass flow rate of oil.

The third aspect of the invention allows accurate determination of the mass flow rate(s) of one or more of the phases in a multiphase flow using just a Coriolis meter, meter, a microwave meter and, optionally, a differential pressure meter installed in situ in a working line. It avoids the need for permanent installation of a radiometric densitometer.

An important advantage of the present invention is that, following calibration of the Coriolis meter and the microwave meter, the accuracy of these meters may be monitored in a simple fashion. As part of a regular, scheduled calibration and/or if a significant change in the flow conditions is believed to have occurred, the performance of these meters may be assessed by taking a sample of the liquid from the multiphase flow in the line, analyzing it to establish the proportions of each liquid phase present, such as oil and water, and comparing this with the WC reading derived from the combination of the Coriolis meter and the microwave meter. As the VF and WC data generated by these two meters are interdependent, if the WC measurement from the meter is accurate, then the VF will also be accurate.

According to a fourth aspect of the invention, a metering arrangement is provided for calculating the mass flow rates of one or more of the phases in a multiphase flow, the metering arrangement comprising:
a) a Coriolis meter for measuring the apparent bulk density and the apparent bulk mass flow rate of the multiphase flow;
b) a differential pressure meter for measuring the differential pressure across the Coriolis meter;
c) a microwave meter, preferably a microwave resonator, for measuring the bulk permittivity of the multiphase flow.

The apparatus according to the fourth aspect of the invention may advantageously comprise a computation device configured to:
a) Calculate a first apparent VF from the apparent bulk density;
b) Calculate a second apparent VF from the bulk permittivity;
c) Calculate the phase volume fractions of the multiphase flow using the results from a) and b);
d) determine the liquid mass flow rate of the multiphase flow using the differential pressure measured by the differential pressure meter;
e) calculate the actual bulk mass flow rate of the multiphase flow;
f) calculate the mass flow rate of one or more of the phases in the multiphase flow.

Advantageously, according to the fourth aspect of the invention calculating the phase volume fractions of the multiphase flow in step c) includes using a first and a second VF error curve correlating the first apparent VF and the second apparent VF to the actual VF determined using a radiometric densitometer.

According to the fourth aspect of the invention, the computation device may be located proximate to the metering arrangement or it may be located remotely from the metering arrangement. In either case, the connection between the metering arrangement and the computation device may be hard-wired or it may operate wirelessly.

The computation device according to preferred embodiments is described as configured or arranged to, or simply "to" carry out certain functions. This configuration or arrangement could be by use of hardware or middleware or any other suitable system. In preferred embodiments, the configuration or arrangement is by software.

Thus according to one aspect there is provided a program which, when loaded onto at least one computer configures the computer to become the computation device.

According to a further aspect there is provided a program which when loaded onto the at least one computer configures the at least one computer to carry out the method steps according to any of the preceding method definitions or any combination thereof.

In general the computer may comprise the elements listed as being configured or arranged to provide the functions defined. For example this computer may include memory, processing, and a network interface.

The invention may be implemented in digital electronic circuitry, or in computer hardware, firmware, software, or in combinations of them. The invention may be implemented as a computer program or computer program product, i.e., a computer program tangibly embodied in a non-transitory information carrier, e.g., in a machine-readable storage device, or in a propagated signal, for execution by, or to control the operation of, one or more hardware modules.

A computer program may be in the form of a stand-alone program, a computer program portion or more than one computer program and may be written in any form of programming language, including compiled or interpreted languages, and it may be deployed in any form, including as a stand-alone program or as a module, component, subroutine, or other unit suitable for use in a data processing environment. A computer program may be deployed to be executed on one module or on multiple modules at one site or distributed across multiple sites and interconnected by a communication network.

Method steps of the invention may be performed by one or more programmable processors executing a computer program to perform functions of the invention by operating on input data and generating output. Apparatus of the invention may be implemented as programmed hardware or as special purpose logic circuitry, including e.g., an FPGA (field programmable gate array) or an ASIC (application-specific integrated circuit).

Figure 1:
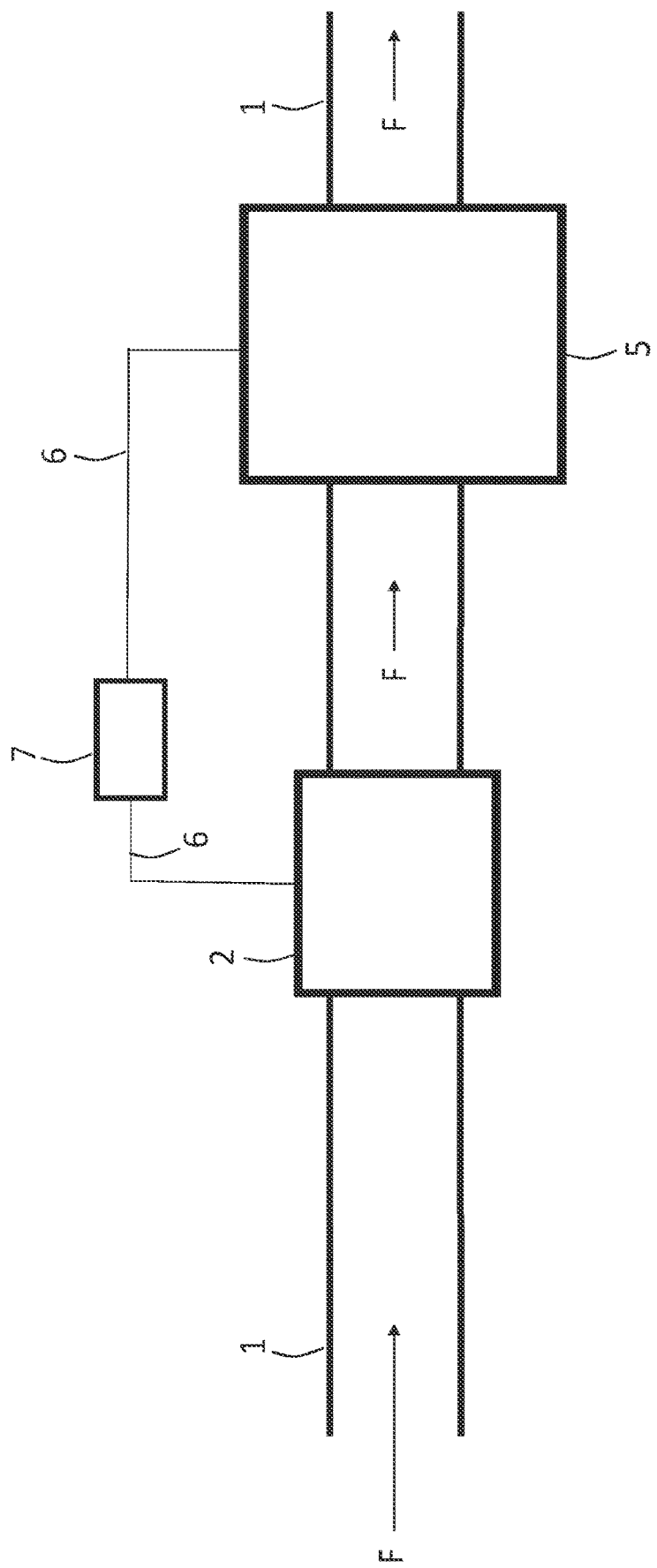
FIG. 1 illustrates an arrangement according to the invention in calibration mode, which enables a device, such as a Coriolis meter or a microwave meter, to be calibrated by means of a radiometric densitometer.

The drawings will now be discussed in more detail:

FIG. 1 figuratively illustrates an arrangement for calibrating a device which measures the property of a multiphase flow from which an apparent VF may be calculated, such as a Coriolis meter or a microwave meter. The calibration is by means of a radiometric densitometer. The arrangement comprises a flow line 1 through which a multiphase flow F passes. The device 2 and a radiometric densitometer 5 are installed in the flow line 1. Instrumentation lines 6 connect each of the device 2 and the radiometric densitometer 5 with a computational device 7. It is possible to perform the calibration on more than one device 2 at a time. For example, two devices 2, such as a Coriolis meter and a microwave meter, may be placed in the flow line 1 and both may be calibrated using the radiometric densitometer 5. Such calibrations may be performed simultaneously or one after the other.

If the device 2 is a Coriolis meter, then the property that it measures is the apparent density of the multiphase flow, F. For completeness, a Coriolis meter may also measure the apparent mass flow of the multiphase flow. The radiometric densitometer 5 measures the actual density of the multiphase flow. If the radiometric densitometer is a dual energy device, then it may also directly determine the actual VF of the multiphase flow, F. The readings from both meters are fed to the computation device 7 which calculates the apparent VF using the apparent bulk density measurement from the Coriolis meter. If necessary (if the radiometric densitometer is not a dual energy device), the computational device 7 also calculates the actual VF using the actual bulk density measurement from the radiometric densitometer. The computational device 7 may also generate a density error curve allowing correction of the apparent bulk density, as measured by the Coriolis meter 2, to the actual bulk density, as measured by the radiometric densitometer.

If the device 2 is a microwave meter, then the property that it measures is the bulk permittivity of the multiphase flow, F. Again, the radiometric densitometer 5 measures the actual density of the multiphase flow, F. The readings from both meters are fed to the computation device 7 which calculates the apparent VF using the bulk permittivity measurement from the microwave meter. If necessary (if the radiometric densitometer is not a dual energy device), the computational device 7 also calculates the actual VF using the actual bulk density measurement from the radiometric densitometer.

Figure 3:
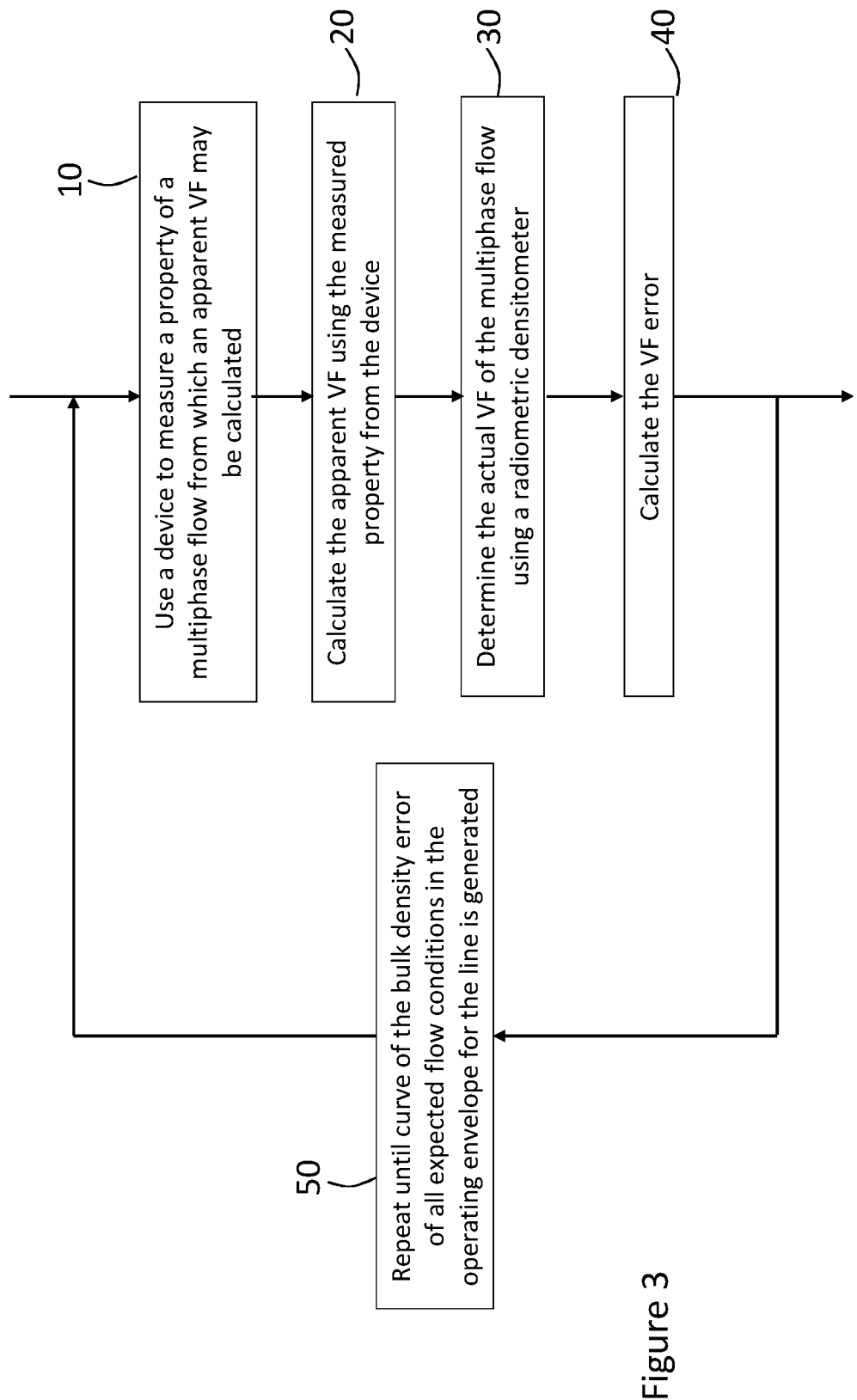
FIG. 3 is a flow chart illustrating the method of the first aspect of the invention.

The arrangement of FIG. 1 functions as shown in the flow diagram of FIG. 3. At 10, a device 2 is used to measure a property of a multiphase flow, F, from which an apparent VF may be calculated. At 20, an apparent VF is measured using the device. At 30 the actual VF of the multiphase flow, F, is determined using a radiometric densitometer. At 40 the error in the VF error is calculated, which is the difference between the actual VF, measured by the radiometric densitometer 5, and the apparent VF, measured by the device 2. These steps are repeated for all expected flow conditions at 50 in order to generate a VF error curve for the entire operating envelope of the line in question.

Figure 2:
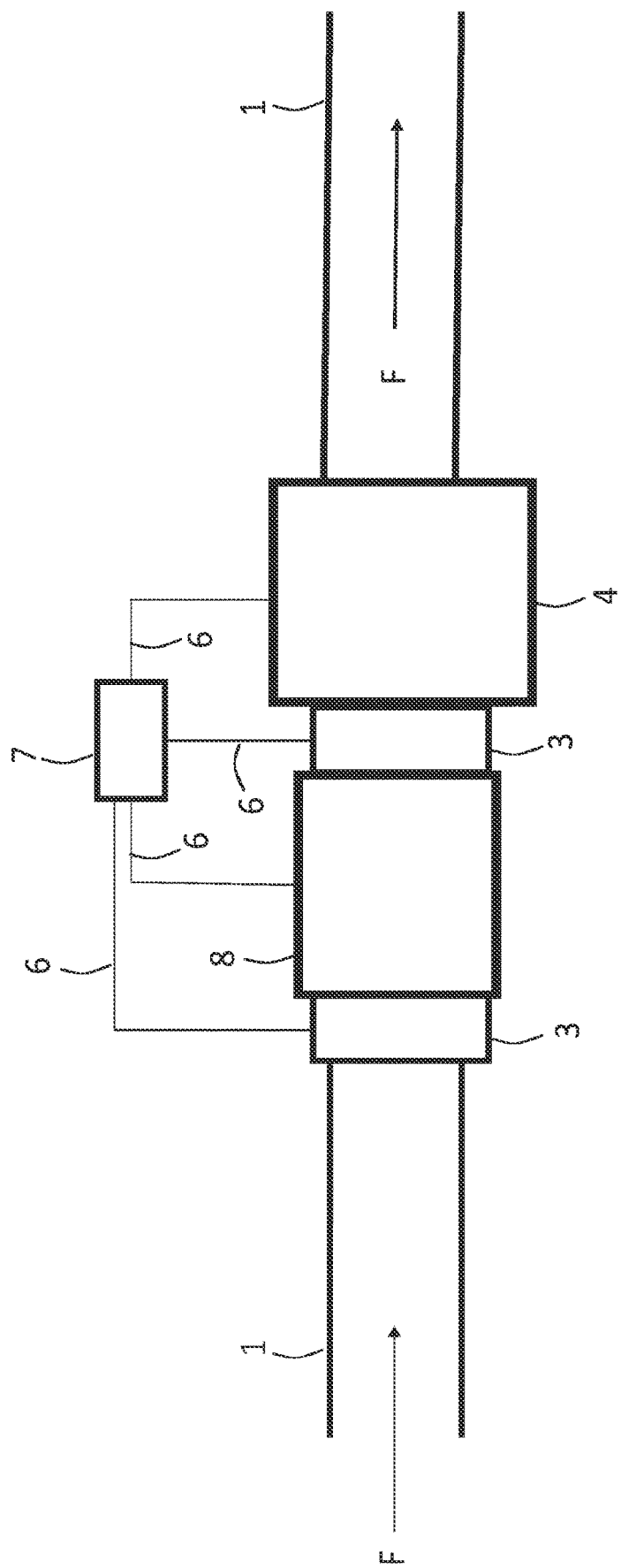
FIG. 2 illustrates a metering arrangement according to the invention in an in-use mode for measuring the mass flow rate of one or more of the phases in a multiphase flow.

FIG. 2 figuratively illustrates an arrangement for measuring the mass flow rate of one or more of the phases in a multiphase flow F in an in-use condition following calibration using the arrangement of FIG. 1. The arrangement of FIG. 2 comprises a flow line 1 through which a multiphase flow F passes. A Coriolis meter 8 has been installed in the line and, either side of the Coriolis meter 8, is a pressure sensor 3, which together measure the differential pressure across the Coriolis meter 8. In addition, a microwave meter 4 is installed in the flow line 1. Instrumentation lines 6 connect each of the Coriolis meter 8, the pressure sensors 3 and the microwave meter 4 with a computational device 7. In this arrangement, the VF error curves for the Coriolis meter 8 and the microwave meter 4 and a bulk density error curve for the Coriolis meter 8 have previously been produced using the arrangement according to FIG. 1 and are stored in computational device 7. Computational device 7 is therefore able to correct the apparent VF measured by both the Coriolis meter 8 and the microwave meter 4 to the actual VF, as previously measured by the radiometric densitometer 5. It may also store a bulk density error curve allowing correction of the apparent bulk density measured by the Coriolis meter 8 to the actual bulk density, as also previously measured by the radiometric densitometer 5, and thereby calculate the actual bulk density of the multiphase flow.

Figure 4:
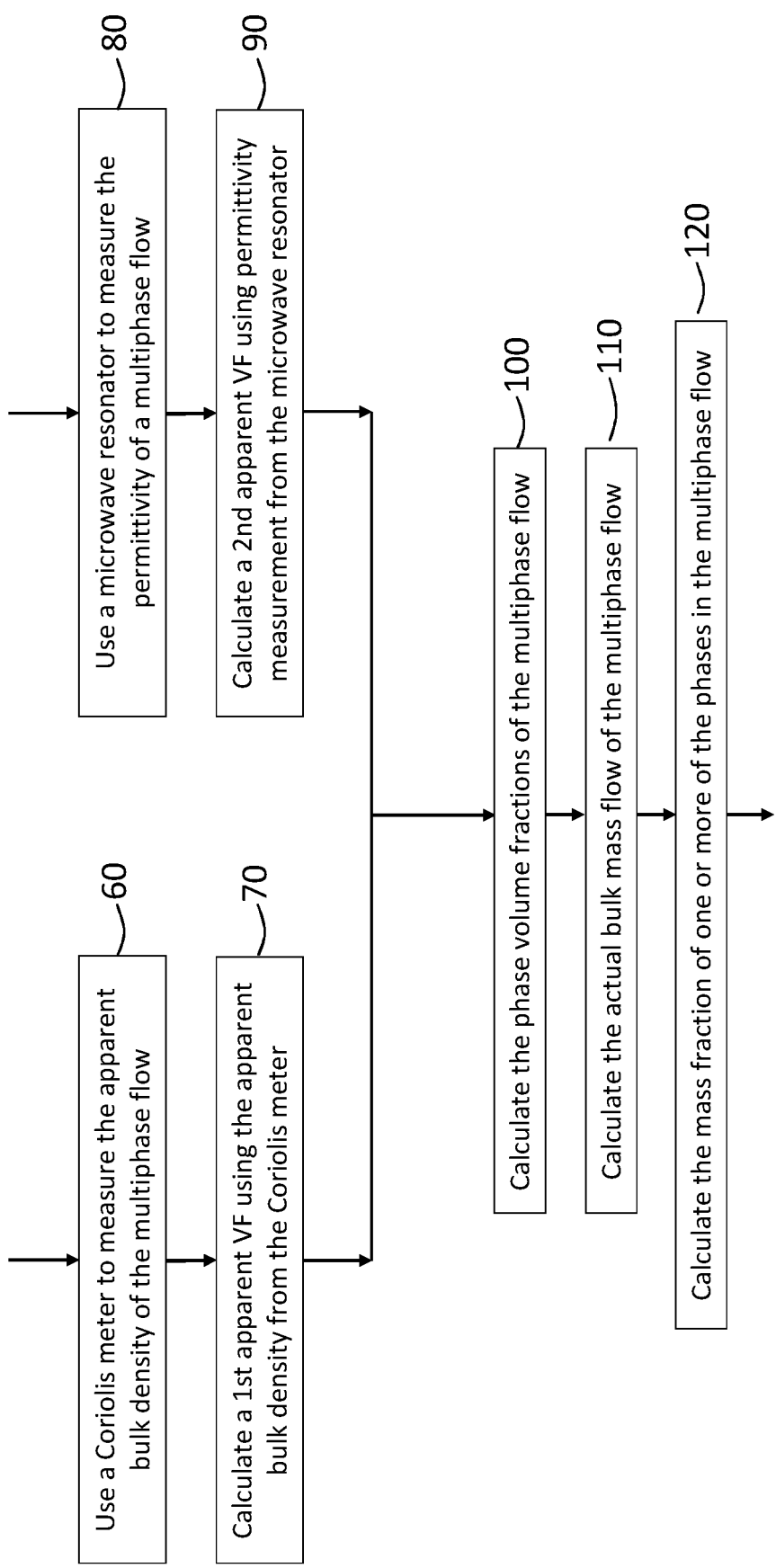
FIG. 4 is a flow chart illustrating the method of the third aspect of the invention.

The arrangement of FIG. 2 functions as shown in the flow diagram of FIG. 4. At 60 the apparent bulk density is measured by the Coriolis meter 8. In addition, although not shown, the apparent mass flow rate may also be measured. At 70, the first apparent VF of the multiphase flow is calculated using the apparent bulk density measured by the Coriolis meter 8. At 80, the permittivity of the multiphase flow is measured using a microwave meter 4. At 90 the second apparent VF is calculated using the permittivity measurement from the microwave meter. The outputs from 70 and 90 are used to generate the phase volume fractions of the multiphase flow at 100. At 110, the actual bulk mass flow is generated using the output from the pressure sensors. Alternatively, in flow regimes in which the liquid velocity is relatively constant, this may be performed by correcting the apparent bulk mass flow rate measured by the Coriolis meter 8 using the bulk density error curve and determining the bulk mass flow rate error from the bulk density error, in the fashion explained above. Finally, at 120 the mass fraction(s) of one or more of the phases are calculated.

Figure 5:
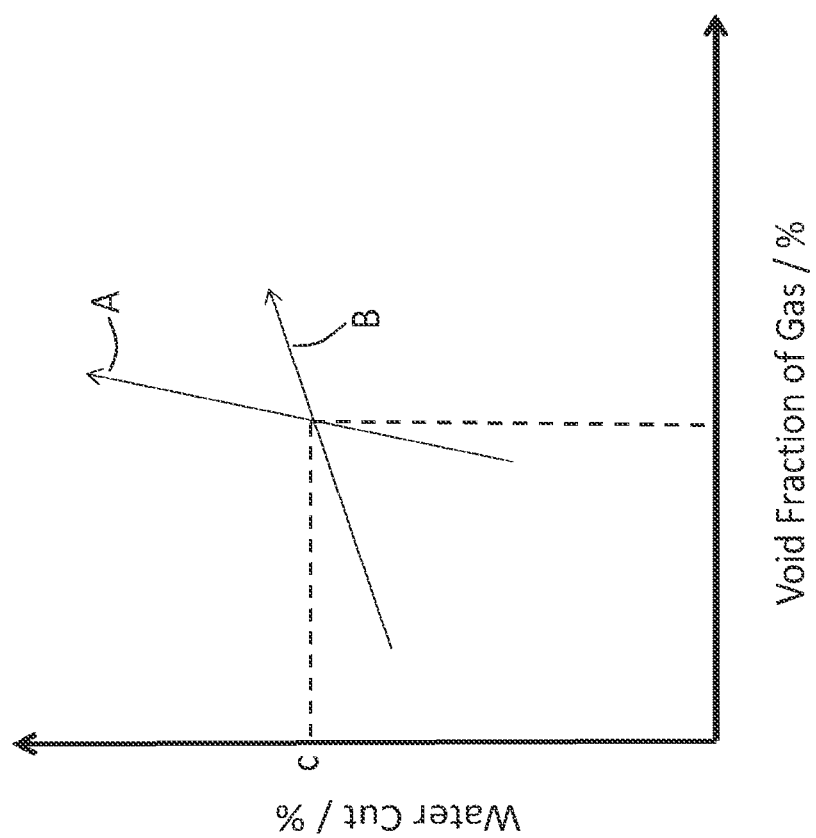
FIG. 5 is a graph showing the relationship between VF and WC for both a Coriolis resonator and a microwave meter.

FIG. 5 is a schematic graph illustrating how the first and second apparent VF data may be used to determine the phase volume fractions:

Curve A, which is the line with the arrow that is in a predominantly vertical direction represents the possible values of VF and WC that correspond to a particular microwave meter mode frequency measurement. This line is in a predominantly vertical direction as this measurement is primarily sensitive to the WC. This is because the electrical permittivity of water is much higher than those of oil and gas, which are similar.

Curve B, which is the line with the arrow that is in a predominantly horizontal direction, represents the possible pairs of VF and WC values that correspond to a particular apparent bulk density value measured by the Coriolis meter. For an assumed water cut value the VF is calculated from Equation 1 which is repeated here for convenience:

$$\text{Apparent } VF = \frac{\rho_L - \rho}{\rho_L - \rho_g} \qquad \text{Equation 1}$$

Where:
$\rho_L$ is the liquid density. This is calculated from the known oil and water densities and the assumed WC
$\rho_G$ is the density of the gas, which is determined from a PVT Model
$\rho$ is the apparent bulk density measured by the Coriolis meter.

This line is predominantly horizontal as this measurement is primarily sensitive to changes in the VF of gas due to the fact that the gas density is much lower than the densities of oil and water.

The method used calculates the VF fraction values that are possible for a range of WC cut values from each measurement (one from the Coriolis meter and one from the microwave meter) and plots these two curves from the results of these calculations. The point at which the two lines cross is the point at which the VF calculated from each measurement is the same. As both lines are monotonic functions (you cannot have the same calculated VF value for two different WC values) the WC at which the lines cross is the actual WC value, marked as point "c" in FIG. 5. This point may be found using either iterative methods or analytically by solving a pair of simultaneous linear equations.

The method described above may become inaccurate if phase contamination occurs. In such a situation, the apparent bulk density measured by the Coriolis meter may become inaccurate. More specifically, the Coriolis meter may over-read the bulk density and a correction is needed to this value to obtain the equivalent VF from the microwave meter. At most VF values, the microwave VF determined from the microwave meter is closer to the actual VF measured by the radiometric densitometer than the VF derived from the Coriolis density data.

Figure 6:
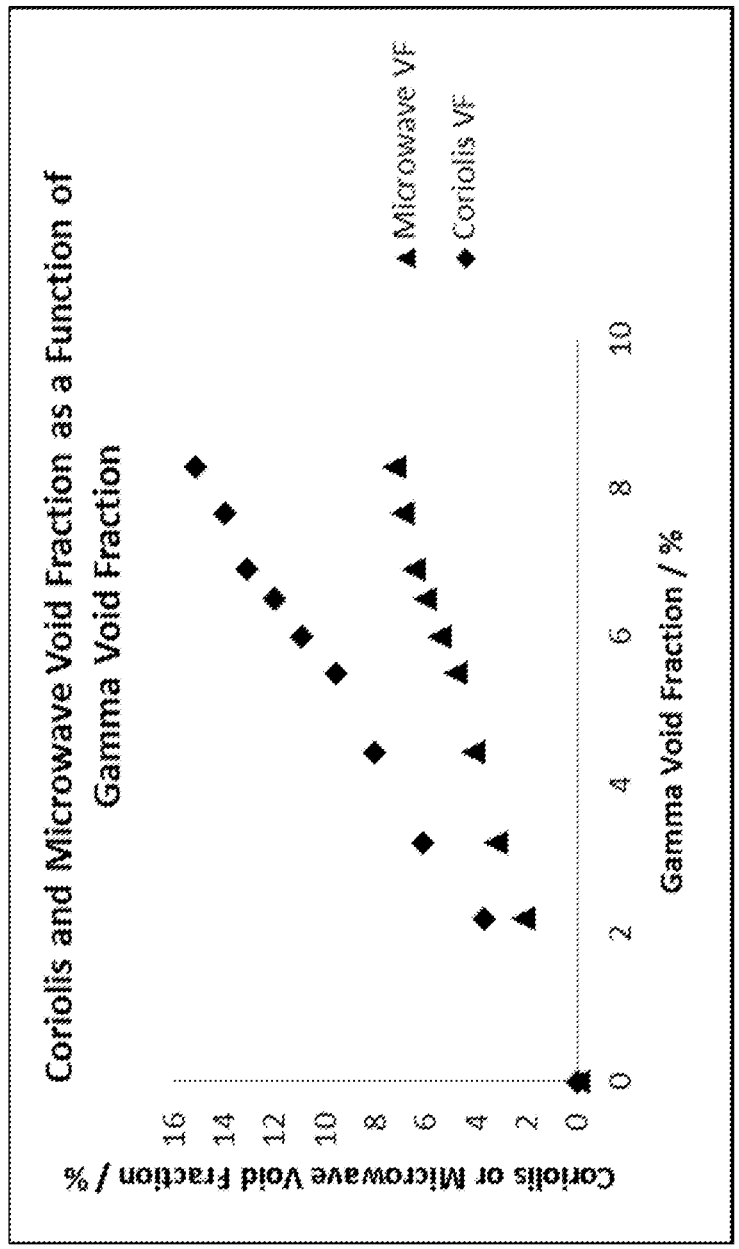
FIG. 6 is a curve showing the GVF measured by the Coriolis meter (y-axis) and microwave meter against the GVF measured by the gamma densitometer (x-axis).

In order to address this situation, a calibration is performed using a radiometric densitometer in order to obtain the error curves between the apparent VF measured by the Coriolis meter and the actual VF measured by the radiometric densitometer on the one hand, and the apparent VF measured by the microwave meter and the actual VF measured by the radiometric densitometer on the other hand. The curves shown in FIG. 6 illustrate the relationships found using the test apparatus described below. Using the error curves, the actual WC of a given multiphase flow may be found by iterating or solving simultaneous equations so that both the measurement from the Coriolis meter and the measurement from the microwave meter yield the actual VF as determined by the radiometric densitometer. This method may give an accurate WC and VF, including in situations in which there is phase contamination.

A test apparatus according to the invention comprised the following devices:
1. An M-Flow Technologies Ltd. microwave resonator
2. An Endress and Hauser Promass Q500, which is a commercially available Coriolis meter suitable for measuring 2 phase liquid flow (such as water-in-oil).
3. Two commercial pressure sensors, one placed either side of the Coriolis meter.
4. A multiphase gamma densitometer manufactured by M-Flow Technologies Ltd. This consists of a gamma source and receiver provided by Berthold Technologies (Berthold LB6775 and source is LB-7440-F-CR) which are mounted outside a piece of composite pipe. The device is a full pipe gamma densitometer (the gamma beam covers the full width of the pipe) and is capable of measuring the line density of the multiphase flow. It is a single energy device.

Devices 1, 2 and 3 were permanently installed parts of the apparatus. Device 4, the gamma densitometer, was installed temporarily to calibrate the density measured by the Coriolis meter.

The relevant test section of the apparatus consisted of a predominantly vertically aligned section in which the microwave resonator, the gamma densitometer and the Coriolis meter were connected in series in the flow path and in this order in the flow direction. In addition, a pressure sensor was connected either side of the Coriolis meter in the flow direction.

Multiphase flow mixtures of water, oil and gas were pumped through the test section in exactly known proportions and the water cut, the VF and the superficial velocities were varied.

The apparent bulk density was measured by the Coriolis meter and the bulk permittivity was measured using the microwave resonator and an apparent VF is derived from both sets of data. At the same time, the actual VF was determined from the gamma densitometer (which is a single energy densitometer) and the relationships between the actual VF, measured by the gamma densitometer, and the apparent VF values determined from the Coriolis apparent bulk density and the microwave permittivity readings were determined. This step was performed for all flow conditions in order to obtain error curves for the entire operating envelope.

The error curves are shown in FIG. 6. At the same time, a bulk density error curve (not shown) was generated, correlating the apparent bulk density measured by the Coriolis meter with the actual bulk density measured by the radiometric densitometer for the entire operating envelope.

After this calibration, the radiometric densitometer was no longer required.

In use, the phase volume fractions were determined as discussed above

To generate an oil mass flow rate, the actual mass flow rate of the multiphase flow must be measured. As previously discussed, this would traditionally be obtained from the Coriolis meter on its own, because one function of this type of meter is to measure mass flow. As also discussed, when a gaseous phase is present in the multiphase flow, the mass flow measurement performance of a Coriolis meter deteriorates and it is challenging to compensate for the errors that occur.

Figure 7:
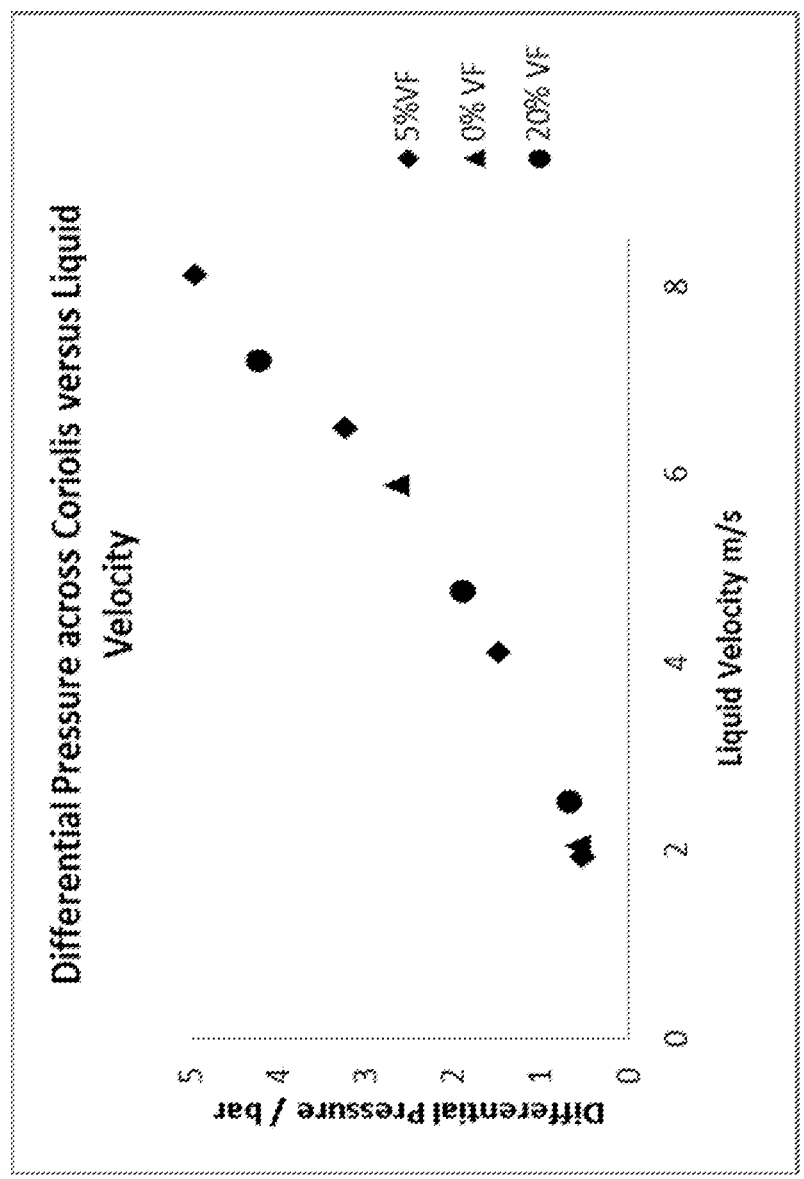
FIG. 7 is a curve showing the differential pressure across the Coriolis meter in bar (y-axis) against the liquid velocity through the Coriolis meter in m/s (x-axis).

The applicant has established that, at low mass percentages of gas, the differential pressure across the Coriolis meter is primarily dependent on the liquid velocity through the meter. Measurements from the test section described above demonstrate this. With reference to FIG. 7, it can be seen that the relationship between differential pressure and liquid velocity is the same for VF of 0%, 5% and 20% (all of which VFs amount to less than 1% by mass of the multiphase flow). In other words, this realization allows one to use the two-phase data to determine three-phase behaviour. By measuring the differential pressure, the liquid mass flow rate of the multiphase flow may therefore readily be determined. Knowing this value, together with the actual bulk density (from the Coriolis meter, corrected using the bulk density error curve) and the pipe diameter, the actual bulk mass flow rate of the multiphase flow at the prevailing temperature and pressure conditions may be calculated.

Finally, the actual mass flow rate of oil is calculated. This is done using the phase volume fractions and the actual bulk mass flow rate. For completeness, the density of each of the individual phases at the given temperature and pressure must also be known, but this is information that the skilled person readily has available.

The invention claimed is:

1. A method of producing a void fraction (VF) error curve which correlates an apparent VF with the actual VF of a multi-phase flow, the method comprising:
   (a) Using a device to measure a property of the multiphase flow from which an apparent VF may be calculated;
   (b) Calculating the apparent VF using the measured property from the device;
   (c) Determining the actual VF of the multiphase flow using a radiometric densitometer;
   (d) Using the values from steps (b) and (c) to calculate the VF error;
   (e) Repeating steps (b) through (d) for all expected flow conditions to generate a VF error curve.

2. A method of calculating the actual VF of a multiphase flow comprising measuring a property of the flow from which an apparent VF may be calculated, calculating the apparent VF of the multiphase flow and correcting the apparent VF using the VF error curve of claim 1.

3. The method of claim 1, wherein the radiometric densitometer is an X-ray densitometer or a gamma densitometer.

4. The method of claim 1, wherein the flow comprises a liquid phase and a gas phase.

5. The method of claim 4, wherein the liquid phase comprises a water phase and an oil phase.

6. The method of claim 1, wherein the device is a Coriolis meter and the measured property is the apparent bulk density of the multiphase flow.

7. The method of claim 1, wherein the device is a microwave meter and the measured property is the permittivity of the multiphase flow.

8. The method of claim 7, wherein the device is a microwave resonator.

9. A method for calculating the mass flow rate of one or more of the phases in a multiphase flow comprising:
- (a) Using a Coriolis meter to measure an apparent bulk density of the multiphase flow;
- (b) Calculating a first apparent VF using the apparent bulk density from step (a)
- (c) Using a microwave meter to measure a permittivity of the multiphase flow;
- (d) Calculating a second apparent VF using the permittivity measurement from step (c);
- (e) Calculating phase volume fractions of the multiphase flow using the results from steps (b) and (d), wherein the VF error curve produced according to claim 1 is additionally used to improve the calculation;
- (f) Determining the actual bulk mass flow rate of the multiphase flow; and
- (g) Calculating the mass flow rate of one or more of the phases using the values from steps (d) and (e).

10. The method of claim 9, wherein the multiphase flow comprises a liquid phase and a gas phase.

11. The method of claim 9, wherein the multiphase flow comprises oil and the method comprises calculation of the oil phase mass flow rate.

12. The method of claim 9, wherein step (f) determining the actual bulk mass flow rate comprises:
- (i) measuring the differential pressure across the Coriolis meter using a differential pressure meter;
- (ii) determining the liquid mass flow rate through the Coriolis meter using the differential pressure value from step (i); and
- (iii) Using the liquid mass flow rate from step (ii), the known phase volume fractions and the actual bulk density of the multiphase flow to calculate the actual bulk mass flow rate;

wherein the actual bulk density is calculated by correcting the apparent bulk density using a bulk density error curve.

13. The method of claim 9, wherein step (e) determining the actual bulk mass flow rate for a multiphase flow comprises:
- (i) determining the bulk mass flow rate error from the bulk density error; and
- (ii) calculating the actual bulk mass flow rate by correcting the apparent bulk mass flow rate using the bulk mass flow rate error, wherein the actual bulk density is calculated by correcting the apparent bulk density using a bulk density error curve.

14. The method of claim 9, wherein the device is a microwave resonator.

15. A metering arrangement for measuring the mass flow rate of one or more of the phases in a multiphase flow, the metering arrangement comprising:
- (a) a Coriolis meter for measuring the apparent bulk density and the apparent bulk mass flow rate of the multiphase flow;
- (b) a differential pressure meter for measuring the differential pressure across the Coriolis meter;
- (c) a microwave meter for measuring the bulk permittivity of the multiphase flow; and
- (d) a computation device to:
    - (i) Calculate a first apparent VF from the apparent bulk density;
    - (ii) Calculate a second apparent VF from the bulk permittivity;
    - (iii) Calculate the phase volume fractions of the multiphase flow using the results from steps (i) and (ii);
    - (iv) determine the liquid mass flow rate of the multiphase flow using the differential pressure measured by the differential pressure meter;
    - (v) calculate the actual bulk mass flow rate of the multiphase flow;
    - (vi) calculate the mass flow rate of one or more of the phases in the multiphase flow.

16. The apparatus of claim 15, wherein calculating the phase volume fractions of the multiphase flow in step (iii) includes using a first and a second VF error curve correlating the first apparent VF and the second apparent VF to the actual VF determined using a radiometric densitometer.

17. The apparatus of claim 16, wherein the computation device is located proximate to or remotely from the metering arrangement.

18. The metering arrangement of claim 15, wherein the microwave meter is a microwave resonator.

* * * * *